US00PP34408P2

(12) United States Plant Patent
Arts

(10) Patent No.: US PP34,408 P2
(45) Date of Patent: Jul. 5, 2022

(54) ***VERONICA* PLANT NAMED 'VVQRA06-0'**

(50) Latin Name: *Veronica longifolia*
Varietal Denomination: 'VVQRA06-0'

(71) Applicant: Agriom Trade BV, de Kwakel (NL)

(72) Inventor: Niels Arts, Aalsmeer (NL)

(73) Assignee: Agriom Trade B.V.

( * ) Notice: Subject to any disclaimer, the term of this patent is extended or adjusted under 35 U.S.C. 154(b) by 0 days.

(21) Appl. No.: 17/402,017

(22) Filed: Aug. 13, 2021

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson
(74) *Attorney, Agent, or Firm* — Cassandra Bright

(57) ABSTRACT

A new and distinct variety of *Veronica* plant named 'VVQRA06-0' is disclosed, characterized by inflorescences of bright pink flowers on compact plants. Plants do not require vernalization for flowering. Plants are day-length neutral and bloom continuously. Plants are hardy in USDA Zones 4 through 8. The new variety is a *Veronica*, typically produced as a garden or container plant.

2 Drawing Sheets

Figure 1:
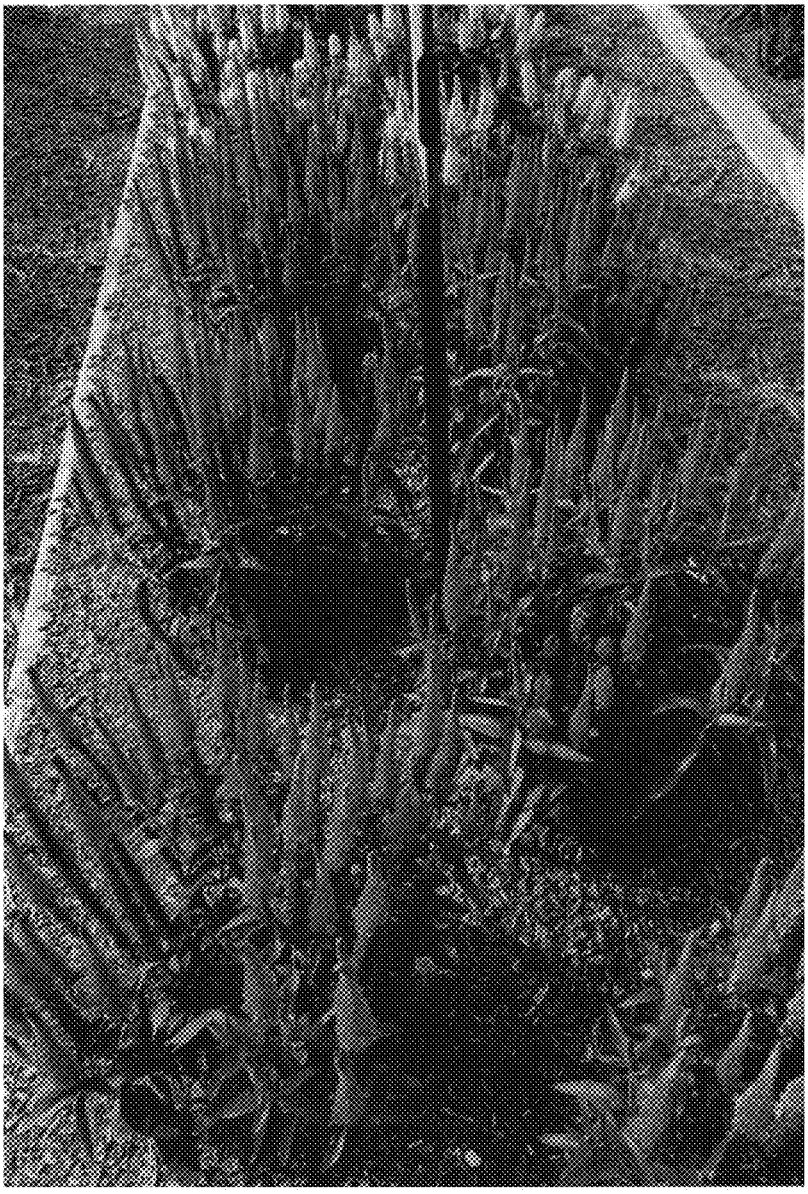

Latin name of the genus and species: *Veronica longifolia*.
Variety denomination: 'VVQRA06-0'.

BACKGROUND OF THE INVENTION

The new cultivar is a product of a planned breeding program. The new variety originated as the result of the crossing of the female parent, an unnamed, unpatented, proprietary *Veronica* and the pollen parent, a different unpatented proprietary *Veronica* referred to as '13-130-002'. The crossing was made during July 2017 at a commercial greenhouse in Santa Paula, Calif. 'VVQRA06-0' was discovered and selected at a commercial greenhouse in Santa Paula, Calif., in December of 2018.

Asexual reproduction of the new cultivar 'VVQRA06-0' was first performed in Santa Paula, Calif. at a research greenhouse by vegetative terminal cuttings in January of 2019. 'VVQRA06-0' has since produced several generations and has shown that the unique features of this cultivar are stable and reproduced true to type.

SUMMARY OF THE INVENTION

The cultivar 'VVQRA06-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VVQRA06-0'. These characteristics in combination distinguish 'VVQRA06-0' as a new and distinct *Veronica* cultivar:

1. Compact plant, forming a low mound.
2. Continuous flowering through Summer.
3. Bright pink flowers.
4. First year flowering. No vernalization requirement.
5. Hardy in USDA Zones 4 through 8.
6. Day-length neutral.

PARENTAL COMPARISON

Plants of the new cultivar 'VVQRA06-0' are comparable to the seed parent in most horticultural characteristics; however, the new variety 'VVQRA06-0' differs in the following:

1. Plants of the new variety are more compact than plants of the seed parent.
2. Plants of the new variety have a darker pink flower than the seed parent variety.

Plants of the new cultivar 'VVQRA06-0' are comparable to the pollen parent in most horticultural characteristics; however, the new variety 'VVQRA06-0' differs in the following:

1. The new variety produces longer inflorescences than the pollen parent.

COMMERCIAL COMPARISON

Plants of the new cultivar can be compared to the unpatented commercial variety *Veronica* 'Skyler Pink'. These varieties are similar in most horticultural characteristics; however, the new cultivar differs in the following:

1. Comparator flower color is a lighter pink/lavender color; the new variety produces dark pink flowers.
2. Plants of the comparator variety are significantly taller than plants of the new variety.

Plants of the new cultivar 'VVQRA06-0' are comparable to the commercial *Veronica* variety 'Pink Passion', U.S. Plant Pat. No. 32,360. The two *Veronica* varieties are similar in most horticultural characteristics; however, the new variety 'VVQRA06-0' differs in the following:

1. Plants of the new variety are taller and narrower than plants of this comparator.
2. Flower color of the new variety is darker pink than flower color of this comparator.

BRIEF DESCRIPTION OF THE PHOTOGRAPHS

The accompanying photograph in FIG. 1 illustrates in full color typical plants of 'VVQRA06-0' grown outdoors in Santa Paula, Calif. These plants are approximately 12 weeks old, growing in the ground.

Figure 2:
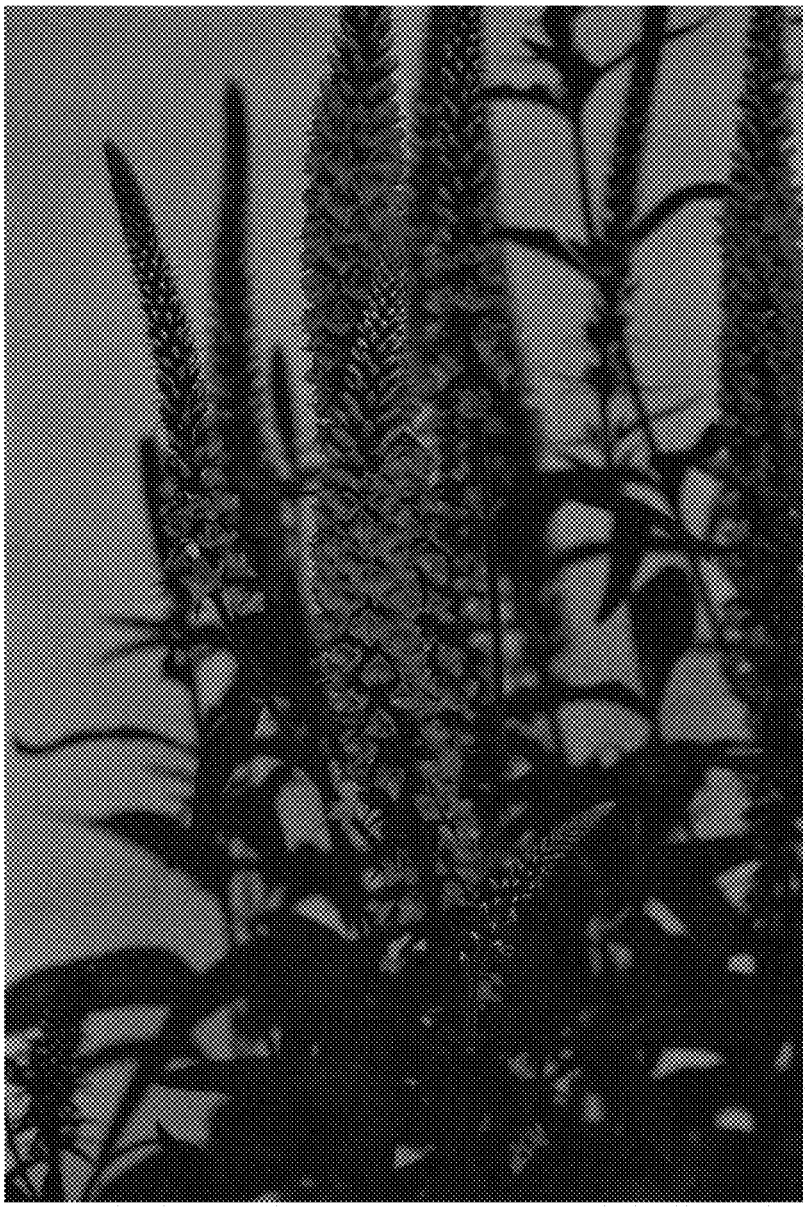

FIG. 2 illustrates a close-up view of the inflorescences.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'VVQRA06-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types. Plants are approximately 7 months old from a rooted cutting.

Botanical classification: *Veronica longifolia* 'VVQRA06-0'.

PROPAGATION

Time to initiate roots: About 18 days at approximately 20° C.

Root description: Vigorous rooting. Root system is larger than above ground plant. Fibrous. Tan to brown, not accurately measured with RHS chart.

PLANT

Plant type: Harding flowering perennial.
Growth habit: Mounding and upright.
Pot size of plant described: 6 inch.
Height: About 30 to 40 cm.
Plant spread: About 20 cm.
Growth rate: Rapid, with no vernalization requirement.
Branching characteristics: Strong basal branching. Average range 3 to 5 main stems/branches per individual plant.
Length of primary lateral branches: About 15 to 20 cm.
Diameter of lateral branches: Approximately 3 to 6 mm.
Texture of lateral branches: Smooth.
Shape of branch/stem: Round, developing to be slightly quadrangular with maturity.
Internode length: 2 to 4 cm.
Strength of stem: Very strong.
Color of lateral branches: Near RHS Green 137B.
Aspect/angle of branches: Very upright, acute angle. Straight.
Number of leaves per lateral branch: Approximately 10 to 12 pairs (over 30 cm of stem).

FOLIAGE

Leaf:
- *Arrangement.*—Opposite (in pairs). Simple.
- *Quantity.*—Approximately 10 to 12 fully expanded per stem.
- *Average length.*—5.5 cm.
- *Average width.*—15 mm.
- *Shape of blade.*—Lanceolate.
- *Apex.*—Acute.
- *Base.*—Clasping.
- *Attachment.*—Sessile.
- *Margin.*—Entire.
- *Texture of top surface.*—Sparsely pubescent.
- *Texture of bottom surface.*—Smooth.
- *Pubescence.*—None.
- *Color.*—Young foliage upper side: Near RHS Green 137B. Young foliage under side: Near RHS Green 137C. Mature foliage upper side: Near RHS Green 137A. Mature foliage under side: Near RHS Green 137B.
- *Venation.*—Type: Linear. Venation color upper side: Near RHS Green 143C. Venation color under side: Near RHS Green 143D.

FLOWER

Natural flowering season: Continuous flowering from late Spring until Fall.

Inflorescence:
- *Arrangement.*—Terminal raceme. Narrow triangular in shape.
- *Inflorescence height.*—12 cm to 15 cm.
- *Inflorescence width.*—1.7 cm.
- *Quantity of flowers per inflorescence.*—Approximately 100 to 120. Moderate density.
- *Typical quantity of inflorescence per plant.*—40 to 60, at once time.
- *Lastingness.*—Individual inflorescences last about 2 months, depending upon environmental conditions.

Individual flower form/shape: Campanulate.

Flower:
- *Diameter of entire flower.*—Approximately 1 cm.
- *Length of flower.*—Approximately 0.7 cm.
- *Aspect.*—Outwardly facing.

Petals:
- *Quantity.*—4.
- *Arrangement.*—Cruciform, fused at the base.
- *Length.*—0.5 cm.
- *Width.*—0.2 cm.
- *Shape.*—Broadly linear.
- *Apex.*—Rounded.
- *Base.*—Fused.
- *Margin.*—Entire.
- *Texture, upper and lower surfaces.*—Glabrous.
- *Appearance upper and lower surfaces.*—Matte.
- *Color.*—When opening, upper surface: Near RHS Red-Purple 71B. When opening, lower surface: Near RHS Red-Purple 71B. Fully opened, upper surface: Near RHS Red-Purple 67A. Fully opened, lower surface: Near RHS Red-Purple 70C.
- *Corolla tube.*—Length: 3 mm. Color: Interior: Near RHS Red-Purple 67A. Exterior: Near RHS Red-Purple 67A.

Calyx/sepals:
- *Shape.*—4 lobes fused at base to form a tube.
- *Apex.*—Acute.
- *Base.*—Fused.
- *Length.*—Total length approximately 4 mm, lobes 1-2 mm.
- *Width.*—Approximately 2-3 mm.
- *Texture.*—Finely pubescent.
- *Color.*—RHS Green 138B.

Peduncle:
- *Peduncle length.*—Approximately 2.0 to 5.0 cm.
- *Peduncle diameter.*—Approximately 3 mm.
- *Color.*—Between RHS Green 138A.
- *Peduncle texture.*—Finely pubescent.
- *Strength.*—Very strong.

Pedicels:
*Pedicel length.*—Approximately 2 mm.
*Pedicel diameter.*—Approximately 1 mm.
*Angle.*—Approximately 45° from attachment.
*Color.*—Between RHS Green 138A.
*Pedicel texture.*—Finely pubescent.
*Strength.*—Flexible, strong.
Bracts:
*Shape.*—Narrow deltoid.
*Length.*—10 to 15 mm.
*Width.*—Approximately 3-5 mm.
*Texture.*—Finely pubescent.
*Color.*—RHS Green 138A.
Bud:
*Shape.*—Elongated ovate.
*Length.*—Approximately 4 to 5 mm.
*Diameter.*—Approximately 2.5 mm.
*Color.*—Near Red-Purple N66C.
*Texture.*—Glabrous.
Fragrance: None.

REPRODUCTIVE ORGANS

Stamens:
*Number.*—2.
*Filament.*—Length: 0.8 cm. Color: RHS Red-Purple 65B.
*Anthers.*—Shape: Oblong. Length: 2 mm. Color: RHS Red-Purple 59D. Pollen: Not observed.
Pistil:
*Number.*—1.
*Length.*—Approximately 2.5 cm.
*Style.*—Number: 2. Length: Approximately 8 mm. Color: Near RHS Red-Purple 59B.
*Stigma.*—Length: About 1 mm. Shape: Linear. Color: Near RHS Red-Purple 59B.
*Ovary.*—Diameter: About 3 mm. Length: About 4 mm. Color: Near RHS Yellow-Green 144C.

OTHER CHARACTERISTICS

Seeds and fruits: Not observed to date.
Disease/pest resistance: Neither resistance nor susceptibility to the normal diseases and pests of *Veronica* has been observed.
Temperature tolerance: USDA zones 4 through 8 tolerant.

What is claimed is:
1. A new and distinct cultivar of *Veronica* plant named 'VVQRA06-0' as herein illustrated and described.

* * * * *